United States Patent [19]
Engström et al.

[11] Patent Number: 5,965,888
[45] Date of Patent: Oct. 12, 1999

[54] PREDICTION OF THE PROPERTIES OF BOARD BY USING A SPECTROSCOPIC METHOD COMBINED WITH MULTIVARIATE CALIBRATION

[75] Inventors: Björn Engström; Mona Hedqvist, both of Sundsvall, Sweden

[73] Assignee: Casco Products AB, Stockholm, Sweden

[21] Appl. No.: 08/981,590

[22] PCT Filed: Jul. 2, 1996

[86] PCT No.: PCT/SE96/00892

§ 371 Date: Dec. 31, 1997

§ 102(e) Date: Dec. 31, 1997

[87] PCT Pub. No.: WO97/04299

PCT Pub. Date: Feb. 6, 1997

[30] Foreign Application Priority Data

Jul. 14, 1995 [SE] Sweden ................................. 9502611

[51] Int. Cl.⁶ ..................................................... G01N 21/17
[52] U.S. Cl. .............................. 250/339.09; 250/339.07; 250/339.11
[58] Field of Search .................. 250/339.09, 339.11, 250/339.07

[56] References Cited

U.S. PATENT DOCUMENTS

| | | | |
|---|---|---|---|
| 4,800,279 | 1/1989 | Hieftje et al. | 250/255 |
| 5,360,972 | 11/1994 | DiFoggio et al. | 250/339.12 |
| 5,536,942 | 7/1996 | Barringer et al. | 250/339.12 |

FOREIGN PATENT DOCUMENTS 0701116  3/1996  European Pat. Off. .

OTHER PUBLICATIONS

Meder et al., "Prediction of Wood Chip and Pulp and Paper Properties Via Multivariate Analysis of Spectral Data", Abstract No. 00393878, 48th Appita Annual General Conference, Melbourne, Australia, May 1994.

Meder et al., "Prediction of Wood Chip and Pulp and Paper Properties Via Multivariate Analysis of Spectral Data", Abstract No. 0572677, 48th Appita Annual General Conference, Melbourne, Australia, May 1994.

P. Niemz et al., "Orientierende Untersuchungen zur . . . " *Holtz als Roh–und Werkstoff* 50 (1992) 25–28.

C. Kniest, "Charakterisierung von Span–Leim–Gemischen . . . " *Holtz als Roh–und Werkstoff* 50 (1992) 73–78.

S. D. Brown, "Chemometrics" *Anal. chem.* 1990 62:84R–101R.

*Primary Examiner*—Constantine Hannaher
*Attorney, Agent, or Firm*—Burns, Doane, Swecker & Mathis, L.L.P.

[57] ABSTRACT

A method for determination of parameters of wood panels, which comprises analyzing the raw wood material/panels at a moisture content <10% by a spectrometric method giving spectral data, and comparing spectral data with reference data from reference material/panels calibrated to known parameters of panels produced from the reference material or of the reference panel by multivariate analysis. Control of process variables influencing parameters of the panels, which comprises analyzing the material/panels, linking spectral data into a combination with desired parameters, and comparing the combination with reference combinations consisting of reference data from reference material/panels linked with known parameters of the reference material/panels, the reference combinations being calibrated to known variables by multivariate analysis.

25 Claims, No Drawings

PREDICTION OF THE PROPERTIES OF BOARD BY USING A SPECTROSCOPIC METHOD COMBINED WITH MULTIVARIATE CALIBRATION

FIELD OF THE INVENTION

This present invention is directed to a method for qualitative and quantitative determination of various parameters reflecting the properties of particleboard and other wood based panels, more particularly to a spectroscopic method combined with multivariate calibration, performed on the raw wood material flow into a plant comprising a process for production of wood based panels, especially on the dried surface and core particles, for the instantaneous and continuous analysis of the various parameters reflecting the quality of the wood based panel and with the knowledge thereof, optionally determine the process variables.

The invention especially relates to the use of NIR (near-infrared) technique combined with multivariate calibration as a tool for prediction of the properties of particleboard and other wood based panels.

It also relates to method for determination of parameters of a wood based panel by analyzing the wood based panel itself by means of a spectrometric method in combination with multivariate analysis.

BACKGROUND OF THE INVENTION

Particleboard can be produced from dry, fine wood particles that are mixed with binders and formed into a mat, which is then pressed together under high temperature and pressure into a densified board.

Wood raw material of almost any type of species may be used. However, the properties of the finished board, such as, for example, density, glueability etc are dependent upon the properties of the wood.

Sawdust, shavings, chips and shavings from round wood, in this specification and claims, referred to as "particles", are used as wood raw material. Flaking of the round wood takes place in drum flakers, while chips are processed in knifering flakers.

Subsequent to disintegration all wood material is dried down to 2–4% moisture in high capacity dryers. After the drying process the wood particles are screened to the preferred size. Rejected material passes through hammer mills and is fed back to the screening system.

Both the form of the flakes/sawdust and their size distribution are of importance for the board properties.

The most commonly used binder for particleboard and medium density fibre boards (MDF), is urea-formaldehyde resin (UF), but also melamine-urea resin (MUF), phenol resin (PF) and isocyanate resin (MDI) are used to some extent, especially for production of weather resistant board.

Resin, water, hardener and wax emulsion are automatically dosed on weight base. Dosages of the chemicals are calculated on the dry substance in percent of dry wood material. The amounts of binder added varies depending upon the resin type and the quality of board desired.

The dosage of UF resin is normally between 7–10%, MUF-resin between 11–13%, PF resin between 6–8% and MDI resin between 2–5%. The comparatively low dosages of PF and MDI resins reflect the superior binding ability of these resins.

A normal particleboard consists of about 6% moisture, 9% binding agent and other chemicals and 85% wood. In spite of the fact that the totally dominating ingredient is wood, the research and development (R&D) efforts within the particle-board industry has, up to mid 80's almost exclusively been dealing with the binders and the role of the wood has been neglected.

It is well known in the pulp and paper industry that the wood must be stored for a certain time before the production of pulp takes place to avoid quality and process problems. During storage wood undergoes important changes in the chemical composition. For instance, some volatile compounds disappear, the amounts of free and bonded acids increase, unsaturated bonds oxidize, hydrolysis of esters will occur, etc.

The particleboard industry has, however, not paid these facts much attention, but instead concluded that process and quality problems are more likely to stem from variations in the binder quality.

Up to now it has not been possible to establish valid correlations between the analysis result of the wood material and the properties of the board, even though there would seem to be a certain connection between acid content and the processability of wood.

One object of the present invention is to accomplish an on-line, in-line or at-line measuring of the raw wood material flow into the plant, giving the possibility of sorting out unsuitable material before it enters the process line.

Investigations of raw wood particles with the analysis technique according to the present invention have now surprisingly shown very high correlations between measured analysis values of the wood and the board properties, e.g. with the board's content of free formaldehyde, which today is extremely important, considering the very stringent environmental stipulations as well as firmness, and water resistance.

Information on particleboard and the processes for the manufacturing thereof is available in "Modern Particleboard & dry-process fibreboard manufacturing" by Thomas M. Maloney (1993), (cf. especially Chapter 4 and 5), which by reference is incorporated herein in its entirety.

The principles of NIR spectroscopy are described by Williams, P.; Norris,K. (1987): New-Infrared Technology in the Agriculture and Food Industries. AACC, St. Paul/Minn. and Sterk, E.; Luchter, K. (1986): Near Infrared Analyses (NIRA) A Technology for Quantitative and Qualitative Analyses. (Applied Spectroscopy Revues 22:4.), all of which are hereby incorporated by reference.

The use of multivariate data analysis in the characterisation of multi-component systems is presently a field of development. Applied generally to the field of chemistry those statistic methods are also termed chemometrics methods. The technique of chemometrics is more fully explained in S. D. Brown, "Chemometrics", Anal. Chem. 62, 84R–101R (1990), which by reference is incorporated herein in its entirety.

The term "board" includes in this specification and claims the following board types: particleboard, medium density fibre board (MDF), waferboard, oriented strand board (OSB), hardboard and plywood.

Process variables which influence the quality of the board are e.g. the wood raw material, viz. sort of wood, the maturing level, the composition of the particles as well as size and moisture content; the particle generation such as Hombak/Mayer particles; the dryer, its inlet and outlet temperatures, dried particle moisture; screening parameters such as surface and core particles, dust content, fractions, moisture content, particle temperature; glueblender variables such as surface and core particles, scale settings, particle temperature, glue amounts, wax amounts, moisture content, cooling water; forming station variables such as volume weight, thickness etc.; pre-press variables such as press time and temperatures; hot-press variables such as press time, pressure, temperature; cooling variables such as temperature; and sanding variables such as surface fineness.

In the proceedings from the 48th Appita Annual General Conference (held at Melbourne, Australia, 2–6 May 1994) Meder et al present an article entitled "Prediction of wood chip and pulp and paper properties via multivaritate analysis of spectral data" (pages 479–484). According to the conclusive part of the article (page 484) Meder et al have used PCR analysis of FTIR, NIR and NMR spectra of wood chip samples to predict the chemical composition of the chips (i.e. in fact to determine said composition from the spectra), and to attempt (although, as explicitly indicated in the article, not very successfully) to predict some physical properties of Kraft and TMP pulp and paper properties. The article does however not suggest any method for qualitative or quantitative determination of parameters of a wood based panel produced from raw wood material flowing into a process for production of wood based panels, little less any method for controlling any process variables in such a process.

In an article in the scientific magazine "Holz als Roh-und Werkstoff 50 (1992) p 25–28" Niemz et al. states that the quality of the board is influenced by the solid resin content and the relation hardwood/softwood. Niemz et al. use NIR spectroscopy for the quantifying of the portion of urea-formaldehyde resin at chips and the mixing ratio of hardwood to softwood. The aim of the tests as performed are to establish if the process is suitable to prove urea-formaldehyde on glued sawdust and to obtain the mixing ratio hardwood/softwood.

It is also stated in the said article that NIR-technique can be used in combination with a linear multiple regression for on-line and off-line control of wood moisture and for the analysis of chemicals and agriculture products. It is furthermore stated that Norris 1962 for the quantitative analysis of foodstuff and fodder combined NIR with mathematical-statistical methods (chemometrics) which later was used for the quantitative analysis within classical chemistry.

In another article in the same magazine at p 73–78 by Kniest a sawdust-glue mixture is characterized by NIR-spectroscopy in combination with linear multiple regression. However, it is at p 77 item 3, 2nd paragraph stated that the measuring of unglued samples is not possible due to the requested data allocations for the process modelling of each board. [Zur Durchführung o.g. Industrieversuche ist die Messung der zugehörigen unbeleimten Probe aufgrund der f ürdie Prozessmodellierung notwendigen Datenzuordnung zur jeweiligen Spanplatte nicht möglich.]

It is obvious from the said reference that the man skilled in the art did not consider it possible to predict the properties of the board from the unglued particles nor to determine such properties in a non-destroying manner from the produced board, and the problem to find an efficient on-line, in-line or at-line method at the beginning of the process for the determination of the parameters characterising the board remained unsolved.

Relevant parameters defining the properties of board are e.g. density and density profile, internal bond, thickness swelling, absorption, permeability, perforator value, modulus of rapture (MOR), parameters relating to volatile organic compounds (VOC) and emission chamber values.

Density is in this connection the same as volume weight and is normally determined by weighing strips of the board with known volume and dividing the mass with the volume. Values are expressed in $kg/m^3$.

Internal bond (IB) is the property of a given board to resist tension perpendicular to the plane of the board. The result is depending on the resin content and the board density; in both cases almost a linear function.

Thickness swelling is measured by placing a sample of a certain size in water with a temperature of 20 or 23° C. during a period of 2–24h. Thickness of the sample is measured before and after the soaking. The thickness difference is divided by the original thickness and expressed in percent. Thickness swelling is a measure of the board's ability to withstand for example unexpected rain or water based paint etc.

Absorption value is normally performed with the same sample that was used for measuring thickness swelling. The sample is weighed before and after the water exposure. The weight difference is divided by the original weight and expressed in percent. The absorption value can be used to predict the board behaviour under severe conditions.

Permeability value is obtained by sucking air through the sample (the board edges are sealed with wax) and the pressure drop across the board is measured along with the air flow through the sample. The permeability varies over the board surface depending on variations in board density but normally there is a good correlation between average permeability and the formaldehyde emission value. Permeability measures the resistance the formaldehyde has in escaping from the board. Values are expressed in cm/minute.

Perforator value expresses the formaldehyde content of the board at a certain moisture content (6.5%). The formaldehyde is obtained by extracting the board in toluene. The released formaldehyde is absorbed in water and determined photometrically. As could be expected there is a connection between the perforator value and the formaldehyde emission from the board and the perforator method is therefore an approved method in many countries. Values are expressed in mg HCHO/100 g ovendry board.

The Emission chamber method is now accepted all over the world as the most accurate method for determination of formaldehyde release from wood based panels or other materials. The conditions in the chamber are set to simulate the conditions in a normal home. The size of the chamber varies between the countries from 1 $m^3$ to 40 $m^3$. The temperature varies from 23 to 25° C., the load varies from 0.3 $m^2/m^3$ to 1.0 $m^2/m^3$, the relative humidity from 45 to 50% and the air rate exchange from 0.5 to 1.0/hour. The board samples are placed vertically with a certain distance in racks in the chamber. Air samples are taken until a steady state is reached, which normally takes 3 to 10 days. Values are expressed in ppm HCHO or in mg $HCHO/m^3$.

Density profile is a measure of the mat forming function and the function of the press and also of the geometry and mix of the wood particles. The profile is today measured by use of apparatus with X-rays capable of measuring the density for each 0.1 mm from surface to surface. A normal density profile for particleboard shows surface densities of 1100 $kg/m^3$ down to 600 $kg/m^3$ in the core.

Thus, much research work has been done in the past to find a solution to the said problem during the years but no convenient solution has been available until by the present invention.

SUMMARY OF THE INVENTION

The invention is directed to a method for qualitative and quantitative determination of the various parameters reflecting the quality of board and other wood based panels and the variables directing the process may be determined, i.e. controlled, on the basis of said parameters. The invention relates more particularly to a spectroscopic method for the instantaneous and continuous analysis of the various parameters reflecting the quality of board performed on the raw wood material flow, especially dried surface and core particles, or on the wood based panel itself.

It has by the present invention been shown that the properties of board can be predicted and through that, optionally, the parameters directing the board process variables determined by the simultaneous application of NIR spectroscopy and multivariate calibration on the raw wood material flow into the plant, especially the dried surface and core particles.

According to the invention the raw wood material is analyzed while having a moisture content of below 10% by a spectrometric method giving spectral data, whereupon said spectral data are compared with reference spectral data obtained by said spectrometric method from reference raw wood material having a moisture content of below 10%, which reference spectral data have been calibrated to known parameters of wood based panels produced from said reference raw wood material by means of multivariate analysis.

The properties of wood based panels can also be determined by a method according to the same inventive concept comprising the steps of analyzing the wood based panel itself while having a moisture content of below 10% by a spectrometric method giving spectral data, and comparing said spectral data with reference spectral data obtained by said spectrometric method from reference wood based panels having a moisture content of below 10%, which reference spectral data have been calibrated to known parameters of said reference wood based panels by means of multivariate analysis.

According to one embodiment a raw wood material or a wood based panel is analyzed by a spectrometric method giving spectral data, which spectral data is then linked into a combination with one or more process variables, which combination is compared with reference combinations obtained by linking reference spectral data, obtained by said spectrometric method from reference raw wood material or reference wood based panels, with reference process variables, which reference combinations have been calibrated to known parameters of wood based panels produced from said reference raw wood material or to known parameters of said reference wood based panel by means of multivariate analysis. In this context "to link into a combination" means that the combination represents a mathematical function of the spectral data and one or more process variables, the latter thus representing independent variables to the function; this implies that said independent variables usually are to be inserted in some mathematical expression or formula when the dependent variable, i.e. "the combination" is to be determined.

The present invention relates according to one embodiment to the application of NIR-spectroscopy on dried surface or core particles, or both, of board in combination with multivariate analysis of the obtained spectra for calibration of the manufacturing of board.

DETAILED DESCRIPTION OF THE INVENTION

According to the invention it has been shown that it is possible to directly and continuously determine various parameters of board and other wood based panels, especially density, density profile, internal bond, thickness swelling, absorption value, permeability value, perforator value and emission chamber value, by detecting spectra of the raw material of the panels when having a moisture content of below 10%, and translating these spectra into said parameters by means of multivariate calibration technique. This method may be used in order to determine, i.e. control, the process variables of a board manufacturing process. The spectrometric method used may be absorption, reflectance, emission or transmission spectrometry, and is preferably applied within the so-called near-infrared (NIR) wavelength range.

It has particularly been shown that it is possible to directly and continuously detect the absorption or transmittance spectra of the dried surface and core wood particles forming the base of board and by the use of said values at discrete wavelengths from these spectra calculate the various parameters of board.

The objects of the present invention are obtained by analyzing a wood based panel or its raw material having a moisture content of less than 10%, especially dry surface or core particles in the process line by means of a spectrometric method, particularly in a wavelength range within 180–2500 nm, suitably within 400–2500 nm, and especially 1000 nm to 2500 nm and applying chemometric evaluation of the spectrum. The method allows the instantaneous and continuous analysis of the various parameters reflecting the quality of board or other wood based panels and through that, the variables directing the process may be determined.

The method is preferably applied on raw material, and wood based panels made of such material, that have been dried in a dryer, suitably within the board production plant; preferably the wood based panel or the raw material, particularly surface and core particles, have been dried under circumstances known to the man skilled in the art down to a moisture level below 8%, preferable below 4%.

The present invention is advantageous e.g. in that the low moisture contents promotes reproducible measurement results; moisture has otherwise a tendency to block or conceal spectrometric information. It is furthermore belived that volatile compounds of natural or synthetic origin in the raw material or the panel, which could also be blocking or concealing spectrometric information, evaporate from the raw material or the panel as the moisture content is decreased. Thus, by performing the analysis at a rather low moisture content more spectrometric information is taken advantage of, safeguarding more accurate and reproducible measurment results. Regarding the raw material it is of course also a great advantage to analyze the material when being in state as close to the one it is supposed to be in when actually used in the production process, i.e. when it is rather dry.

The wood based panel is preferably a board, suitably a particleboard.

The multivariate analysis performed according to the present invention may be Principal Component Analysis (PCA), Partial Least Squares Regression (PLS), Principal Component Regression (PCR), Multilinear Regression Analysis (MLR) or Discriminant Analysis, preferably Partial Least Squares Regression.

The method according to the present invention may also be applied in a method for controlling process variables influencing parameters of a wood based panel produced from raw wood material flowing into a process for production of wood based panels; in that case the present method may be used to determine the board parameters, which information then is fed into a system for controlling the process. It is also possible is to design a controlling system in which the obtained spectra, optionally after having reduced noise or base line drift, are put in directly into the system for setting the process variables without having translated the spectra into board parameters; this could suitably be accomplished by establishing a calibration model in which process variables are expressed as functions of panel parameters and the spectral data, and then using the model in the actual production, at which spectral data are obtained from the raw material, i.e. feed-forward controlling, or the produced panel, i.e. feed-back controlling, and linked with desired panel parameters to give the required process variables.

According to one embodiment the wood based panel is analyzed while having a moisture content of below 10% by a spectrometric method giving spectral data, and the thus obtained spectral data compared with reference spectral data obtained by said spectrometric method from reference wood based panels made in said process at known process variables, said reference panel having a moisture content of below 10%, parameters of said reference wood based panels being known, which reference spectral data have been calibrated to said known process variables by means of multivariate analysis.

According to another embodiment the raw wood material or the wood based panel is likewise analyzed while having a moisture content of below 10% by a spectrometric method giving spectral data, and said spectral data compared with reference spectral data obtained by said spectrometric method from reference raw wood material used, or reference wood based panels produced from said reference raw wood material, in a reference process for production of wood based panels while having a moisture content of below 10%, which reference spectral data have been calibrated to process variables applied in said reference process, by means of multivariate analysis.

In yet another embodiment the raw wood material or the wood based panel is analyzed, again while having a moisture content of below 10%, by a spectrometric method giving spectral data, the obtained spectral data linked into a combination with at least one desired parameter, and said combination compared with reference combinations obtained by linking reference spectral data, obtained by said spectrometric method from reference raw wood material or reference wood based panels having a moisture content of below 10%, with known parameters of said reference raw wood material or said reference wood based panels, which reference combinations have been calibrated to known process variables by means of multivariate analysis.

Technically, the spectrometric analysis can be performed by on-line, in-line or at-line optical fibre probe, or by taking individual samples for separate analysis. In both cases, the spectra are subject to further data treatment using values from several discrete wavelengths from each particular spectrum. It is to be understood that the radiation used in the spectrometric method impinges directly on raw material or the wood based panel.

The spectral information reflects a variety of properties. Depending on the parameter of interest relevant and selected information is correlated to the specific parameter.

An example of such a technique is the use of a device, placed at a distance from the process, containing a light source, detector, electronic components and other necessary components to transmit a signal through an optical fibre to the sample, where the light is transmitted through or reflected on or partly through the sample. The resulting signals are returned to the detector in an accompanying optical fibre cable, and recorded.

In the spectrometer, the light is converted into an electric signal which is then conveyed to a computer where the spectrum of a previously stored reference scan can be related to, e.g. subtracted from, the sample spectrum and a reference corrected spectrum is calculated.

Another example is by manually or automatically taking samples at relevant time intervals and submitting the samples to analysis in an analytical instrument, containing the light source, detector, electronic components and other necessary components. The absorption or transmittance spectra are then subjected to further data treatment, using values from several discrete wavelengths from each particular spectrum.

It is preferred that the detector has a measuring interval of at the most 10 nm, preferably 2 nm, and most preferably 1 nm or less. The detection is performed in the VIS-NIR wavelength range of 180 nm to 2500 nm.

This can be accomplished by the use of a scanning instrument, a diode array instrument, a Fourier transform instrument or any other similar equipment, known to the man skilled in the art.

An evaluation of wavelengths which contain absorption or transmission provides features relevant for the analysis. By the application of chemometrical methods to the obtained spectra it is then possible to ignore wavelengths which do not contain information that contribute to the chemical analysis, even though the measurement will include information from the entire wavelength range.

The determination and control of the board parameters by use of the spectrometric measurement comprise two main steps, the first of which being the development of a calibration model, involving the substeps of development of learning sets; data processing; and data analysis by the use of surface and core particles having known parameter values. The second main step is the spectrometric analysis of the sample of having unknown parameter values, spectral data processing, optionally followed by data analysis; and application of the calibration model, developed in the first main step, to the thereby obtained data.

One embodiment of the invention is analyzing the near-infrared spectra within a wavelength range of 400–2500 nm, particularly 1000–2500 nm of dried-surface and core particles and applying chemometric evaluation to the spectra to calculate the parameters of the particles such as e.g. density, density profile, internal bond, adsorption, permeability, perforator value, and emission chamber values.

According to a preferred embodiment the present method comprises the steps of (I) developing a calibration model by (I.a) registering, by means of a spectrometric method, reference spectral raw data of reference samples of the reference raw wood material or the reference wood based panel;

(I.b) processing the reference spectral raw data, to reduce noise and adjust for drift and diffuse light scatter;

(I.c) calibrating the processed reference spectral data with the known parameters of the reference samples by performing a data analysis comprising multivariate analysis; and (II) registering, by means of said spectrometric method, spectral raw data of a sample of raw wood material or a wood based panel having unknown parameters;

processing the thereby obtained spectral raw data to reduce noise and adjust for drift and diffuse light scatter; and applying the developed calibration model on the processed spectral data in order to determine the unknown parameters. The multivariate analysis in sub-step (I.c) preferably includes transferring the processed reference spectral data into latent variables; and in sub-step (II) the processed spectral data are preferably transferred into latent variables as according to (I.c), and the developed calibration model applied on the latent variables in order to determine the unknown parameters. The transformation into latent variables by means of Principal Component Analysis (PCA). This preferred embodiment is discussed in more detail below:

(I) Development of a Calibration Model

The board parameters are measured in the traditional way for a number of samples. The values are then used in the development of a calibration model wherein the three sub-steps discussed below are applied to the registered absorption, reflectance or emission spectra of said samples.

(I.a) Development of learning sets

Model learning sets consist of a large number of absorption or transmission spectra from samples with known values that preferably should be representative of the production line. The learning sets are used in the chemometric algorithms to calculate the resulting model parameters.

(I.b) Data processing

To reduce noise and adjust for base line drift the spectral raw data should be processed. This processing may also reveal hidden information, such as identity of apparently dissimilar spectra or non-identity of apparently very similar spectra. Moreover, the assumptions leading to Beer's law (stating that, for a given absorption coefficient and length of the optical path in the absorptive media, the total amount of light absorbed is proportional to the molecular concentration of the sample) are not always fulfilled in the complex system that the samples constitutes. This is due to a number of factors, often found in industrial and laboratory samples. Another complicating factor is light scattering variations, depending on particles in the sample. Various theories have been developed to overcome this problem and the most used are: the Kubelka-Munk transformation (P. Kubelka, F. Munk, Z. Tech. Physik 12, 593 (1931), incorporated herein by reference), which takes account of absorption and scatter; and the Multiplicative Scatter Correction (P. Geladi, D. MacDougall, H. Martens, Appl. Spect. 39, 491–500 (1985), incorporated herein by reference) where each spectrum is 'corrected' in both offset and slope by comparing it to an 'ideal' spectrum (the mean spectrum). Another way of linearising the spectral data also is by use of derivatives, e.g. up to the fourth order derivatives (A. Savitzky, M. J. E. Golay, Anal. Chem. 36, 1627–1639 (1964), incorporated herein by reference). The derivative of the spectrum results in a transformed spectrum, consisting only of the relative changes between the adjacent wavelengths, and it has been shown that the peak intensities of derived spectra tend to be more linear with concentration (T.C. O'Haver, T. Begley, Anal. Chem. 53, 1876 (1981), incorporated herein by reference). Linearisation can also be accomplished by use of the Fourier transformation, or by use of the Standard Normal Variate transformation as disclosed in R. J. Barnes, M. S. Dhanoa and S. J. Lister, Appl. Spectrosc., Vol. 43, number 5, pp. 772–777 (1989), incorporated herein by reference.

(I.c) Data analysis

Data analysis using chemometric techniques then allows the calibration model to be developed. There are several chemometric techniques which can be used, such as Principal Component Analysis (PCA), Partial Least Squares Regression (PLS), Principal Components Regression (PCR), Multilinear Regression Analysis (MLR) and Discriminant Analysis. The preferred chemometric technique according to the invention is the PLS method.

(I.c.1) Principal Component Analysis (PCA)

By PCA, a set of correlated variables is compressed into a smaller set of uncorrelated variables. This transformation consists of a rotation of the coordinate system, resulting in the alignment of information on a fewer number of axes than in the original arrangement. Hereby, the variables that are highly correlated with one another will be treated as a single entity. By using PCA, it thus will be possible to obtain a small set of uncorrelated variables still representing most of the information which was present in the original set of variables, but being far easier to use in models. In general, 2 to 15 principal components will account for 85% to 98% of the variance of the variables.

(I.c.2) Partial Least Squares Regression (PLS)

PLS is a modelling and computational method by which quantitative relations can be established between blocks of variables, e.g. a block of descriptor data (spectrum) for a series of samples and a block of response data measured on these samples. By the quantitative relation between the blocks, it is possible to enter spectral data for a new sample to the descriptor block and make predictions of the expected responses. One great advantage of the method is that the results can be evaluated graphically, by different plots. In most cases, visual interpretations of the plot are sufficient to obtain a good understanding of different relations between the variables. The method is based upon projections, similar to PCA. The PLS method is disclosed in detail in Carlsson R., Design and optimization in organic synthesis, B. G. M. Vandeginste, O. M. Kvalheim, Eds., Data handling in science and technology, (Elsevier, 1992), vol.8, incorporated herein by reference.

(I.c.3) Principal Components Regression (PCR)

PCR is closely related to PCA and PLS. As in PCA, each object in the descriptor block is projected onto a lower dimensional space yielding in scores and loadings. The scores are then regressed against the response block in a least squares procedure leading to a regression model which can be used to predict unknown samples. The same model statistics as in PLS and PCA can be used to validate the model. For an excellent tutorial in PCA, PLS and PCR, see P. Geladi et al in "Partial Least-Squares Regression: A Tutorial" in Anal. Chim. Acta, 185, 1–32 (1986), which is incorporated herein by reference in its entirety.

(I.c.4) Multilinear Regression Analysis (MLR)

By MLR, the best fitting plane for the board parameters as a function of the spectra is defined, using least squares techniques to define each boundary of the plane. This plane is then used to recognize and assign a predicted value to an unknown board parameter value. This technique is generally limited to relatively 'clean' systems where there is not a significant amount of matrix interference and, in contrast to PLS, it requires more objects than variables.

(I.c.5) Discriminant Analysis

This is a method whereby, by use of spectral data, the known board parameter values are grouped into different clusters, separated by linear decision boundaries. From its spectrum, a sample of unknown board parameter values then can be matched to a cluster, and the board parameter value can be assigned a value, e.g. the average value of the cluster. This is a very useful technique for quality screening, but requires a very large data base to obtain statistically significant results.

(II) Determination by Application of the Calibration Model

Once a calibration model has been developed, the determination of the unknown values can be performed by registering the absorption or transmission spectrum, in correspondence to (I.a). Processing the thereby obtained spectral raw data as according to (I.b); optionally performing a data analysis on the processed spectral data as according to (I.c); and applying the developed calibration model to the thereby obtained data.

The invention will now be illustrated by way of examples.

Five test boards were made at the laboratory having different particle composition but the same glue recipe. Three different kinds of raw particles of three different ages (old, 3 months, and fresh) were used. They were dried and screened to surface and core particles at the laboratory. Each age represented one test board and the forth test board represented a mixture of the three other. The fifth test board is a reference sample having surface and core particles from the commercial production. The particle mixtures of the boards are set forth in Table I below. The moisture content of each sample had been analyzed according to standard methods. NIR measurements on each type of particle was performed at AKZO NOBEL Analyscentrum in Nacka, Sweden. The instrument used was a FT-NIR instrument Bomem 160 with drift cell. The particles were placed in a beaker and the samples were scanned 16 times/spectrum between 1000–2500 nm. In addition to the measurements made according to known technique on complete boards also emission measurement with desiccator lids (the EXS-method, as reported below) were tested and also a method wherein the board is placed in a box and air sucked through the board (the BOX-method, as reported below). The results were shown on monitor, Interscans direct instrument for formaldehyde. The measurement, which closest represents an on-line method in the plant was made on cooled raw board, when the air in the desiccator lid had a temperature of 30° C. and should give information whether the formaldehyde measurement on-line is well correlating to the chamber value. The results of said measurements are set forth in Table II below. Sirius program for multivariate data was used to extract further information from the normalized NIR spectra. Response models for the particle variables as well as the board variables were built up with 6 PLS components. The response models could be expressed as Y=KX+M, i.e. an equation describing a straight line in a conventional X-Y coordinate system, where Y is the predicted parameter, X is the actually measured parameter, K is the correlation constant for the response model (indicating the slope of the line), and M indicates the interception of the line with the Y-axis, i.e. the value Y assumes when X has the value of zero in the model. For an ideal response model K is 1 and M is 0. The values of K and M for the different measurements are shown in Table III together with the correlations of the models with the actual values, which for an ideal model is 1, and the average predictive errors. Multiwavelength spectroscopy, carried out on the surface and core particles followed by linearisation of spectral data and multivariate data evaluation (PLS algorithm) were used to determine the board parameter values. The reference samples consisted of in total 10 samples of different origin as reported in the tables and thereby having different parameters. The samples had been dried to a moisture content between 0.9 and 2.3% and screened to surface and core particles.

Surface particle fraction: (0.5–2 mm)
Core particle fraction: (2–8 mm)

One test comprising 2×4 three layer boards were performed for each composition and in the same way a test was made with a mixture of the three compositions in equal parts. One test with surface and core reference particles was made. Urea-formaldehyde resin UF 1155 from Casco Products AB was used in all tests. Four of the boards were combined to a chamber board. Emission measurements were made with desiccator lid as well as air sucking of the board in a box. Complete board testing for each test was performed after the chamber test.

The following abbreviations are used in the tables:

| | |
|---|---|
| Dens. | Density |
| IB | Internal bond |
| TSW 24 h | Thickness swelling |
| ABS 24 h | Absorption |
| PB | Permeability, cm/min. |
| PV | Perforator value photom., mg HCHO/100 g |
| REM | Rapid emission method, mg HCHO/liter |
| Em.kam | Emission chamber, mg HCHO/m$^3$ |
| EXS 30° C. | Desiccator lid 0.82 dm$^2$, with tape as distances against the board. 3 liter air sucked over the board per minute. Newly pressed raw board. Temp. 30° C. |
| EXS 23° C. | Desiccator lid 0.82 dm$^2$ with tape as distances against the board. 3 liter air sucked over the board per minute. Newly pressed raw board. Temp. 23° C. |
| EXS 1d | Desiccator lid 0.82 dm$^2$ with tape as distances against the board. 3 liter air sucked over the board per minute. Rubbed board, 1 day. |
| Box 4d | Air sucked through the board 4.8 dm$^2$, 5 l/min. Rubbed board, taped edges, 4 days. |
| Box 12d | Air sucked through the board 4.8 dm$^2$, 5 l/min. Rubbed board, taped edges, 12 days. |
| Box 27d | Air sucked through the board 4.8 dm$^2$, 5 l/min. Rubbed board, taped edges, 27 days. |
| Box k-sk | Air sucked through the board 4.8 dm$^2$, 5 l/min. Rubbed board, taped edges, measurement on board tested in a chamber |

TABLE I

PARTICLE MIXTURES FOR PRESSING

| Board code | | Age | Moisture % |
|---|---|---|---|
| | Surface particles | | |
| 50185 | Ref. particles | Normal pro- | 2.3 |
| 50186 | Comp. 1 | Old | 4.2 |
| 50187 | Comp. 2 | Fresh | 3.3 |
| 50188 | Comp. 3 | 3 months | 3.5 |
| 50189 | Comp. 1 + 2 + 3 | Mixture | 3.8 |
| | Core particles | | |
| 50185 | Ref. particles | Normal pro- | 2.0 |
| 50186 | Comp. 1 | Old | 2.8 |
| 50187 | Comp. 2 | Fresh | 2.9 |
| 50188 | Comp. 3 | 3 months | 3.2 |
| 50189 | Comp. 1 + 2 + 3 | Mixture | 3.1 |

TABLE II

Board variables to correlate to NIR-measurements on surface and core particles

| Board code | Dens. | IB | TSW 24 h | ABS 24 h | PB | PV | REM | Em.kam |
|---|---|---|---|---|---|---|---|---|
| 50185 | 746 | 1.01 | 8.5 | 24.7 | 1.0 | 5.3 | 2.4 | 0.112 |
| 50186 | 756 | 0.82 | 16.8 | 35.8 | 0.7 | 4.7 | 2.5 | 0.091 |
| 50187 | 751 | 0.66 | 15.5 | 32.1 | 1.2 | 4.2 | 2.4 | 0.076 |

TABLE II-continued

Board variables to correlate to NIR-measurements on surface and core particles

| | | | | | | | | |
|---|---|---|---|---|---|---|---|---|
| 50188 | 760 | 0.76 | 17.2 | 36.5 | 1.3 | 4.5 | 2.6 | 0.081 |
| 50189 | 755 | 0.72 | 18.6 | 39.3 | 0.7 | 4.4 | 2.6 | 0.083 |

| Board code | EXS 30° C. | EXS 23° C. | EXS 1d | PBL-box 4d | PBL-box 12d | PBL-box 27d | PBL-box k-sk |
|---|---|---|---|---|---|---|---|
| 50185 | 0.140 | 0.055 | 0.085 | 0.240 | 0.16 | 0.14 | 0.15 |
| 50186 | 0.070 | 0.055 | 0.055 | 0.225 | 0.19 | 0.17 | 0.16 |
| 50187 | 0.045 | 0.045 | 0.050 | 0.245 | 0.20 | 0.17 | 0.14 |
| 50188 | 0.055 | 0.045 | 0.040 | 0.320 | 0.22 | 0.19 | 0.14 |
| 50189 | 0.045 | 0.040 | 0.045 | 0.330 | 0.22 | 0.20 | 0.16 |

TABLE III

| Parameter | K | M | Correlation | Average Predictive Error |
|---|---|---|---|---|
| Moisture | 0.975 | 0.078 | 0.987 | 0.226 |
| Dens. | 0.908 | 69.403 | 0.953 | 2.578 |
| IB | 0.998 | 0.002 | 0.999 | 0.034 |
| TSW 24 h | 0.996 | 0.057 | 0.998 | 0.467 |
| ABS 24 h | 0.999 | 0.034 | 0.999 | 0.510 |
| PB | 0.872 | 0.125 | 0.934 | 0.148 |
| Em.kam | 0.984 | 0.001 | 0.992 | 0.003 |
| REM | 0.991 | 0.021 | 0.996 | 0.013 |
| PV | 0.997 | 0.016 | 0.998 | 0.103 |
| EXS 30° C. | 0.996 | 0.000 | 0.998 | 0.008 |
| EXS 23° C. | 0.966 | 0.002 | 0.983 | 0.004 |
| EXS 1d | 0.975 | 0.001 | 0.987 | 0.004 |
| Box 4d | 0.980 | 0.006 | 0.990 | 0.017 |
| Box 12d | 0.995 | 0.001 | 0.997 | 0.005 |
| Box 27d | 0.997 | 0.000 | 0.999 | 0.005 |
| Box k-sek | 0.889 | 0.017 | 0.943 | 0.005 |

As can be seen from Table III the slopes K and the correlations are all very close to the ideal value of 1. Most intercepts M are very close to the ideal value of 0, the parameter of density being the exception; in that case, however, it should be noted that the actual values of the measured board ranged from 745 to 760, indicating that the divergence was in fact quite small seen in relation to the actual values, which is also reflected by the small average predictive error in that case.

We claim:

1. A method for qualitative or quantitative determination of parameters of a wood based panel produced from raw wood material flowing into a process line for production of wood based panels, characterized in that the method comprises:
analyzing the raw wood material or the wood based panel while having a moisture content of below 10% by a spectrometric method giving spectral data, and
comparing said spectral data with reference spectral data obtained by said spectrometric method from reference raw wood material or reference wood based panels having a moisture content of below 10%, which reference spectral data have been calibrated to known parameters of wood based panels produced from said reference raw wood material or to known parameters of said reference wood based panel by means of multivariate analysis.

2. A method according to claim 1, characterized in that the method comprises:
analyzing the raw wood material or the wood based panel while having a moisture content of below 10% by a spectrometric method giving spectral data,
linking said spectral data into a combination with a process variable, and
comparing said combination with reference combinations obtained by linking reference spectral data, obtained by said spectrometric method from reference raw wood material or reference wood based panels having a moisture content of below 10%, with reference process variables, which reference combinations have been calibrated to known parameters of wood based panels produced from said reference raw wood material or to known parameters of said reference wood based panel by means of multivariate analysis.

3. A method according to claim 2, characterized in that the wood based panel is a board.

4. A method according to claim 1, characterized in that the raw wood material is analysed, and
the spectral data is compared with reference spectral data obtained from reference raw wood material, which reference spectral data have been calibrated to known parameters of wood based panels produced from said reference raw wood material.

5. A method according to claim 4, characterized in that the wood based panel is a board.

6. A method according to claim 1, characterized in that the wood based panel is analysed, and
the spectral data is compared with reference spectral data obtained from reference wood based panels, which reference spectral data have been calibrated to known parameters of said reference wood based panels by means of multivariate analysis.

7. A method according to claim 6, characterized in that the wood based panel is a board.

8. A method according to claim 1, characterized in that the wood cased panel is a board.

9. A method according to claim 8, characterized in that the board is a particleboard.

10. A method according to claim 1, characterized in (I) developing a calibration model by (I.a) registering, by means of a spectrometric method, reference spectral raw data of reference samples of the reference raw wood material or the reference wood based panel; (I.b) processing the reference spectral raw data, to reduce noise and adjust for drift and diffuse light scatter; (I.c) calibrating the processed reference spectral data with the known parameters of the reference samples by performing a data analysis comprising multivariate analysis; and (II) registering, by means of said spectrometric method, spectral raw data of a sample of raw wood material or a wood based panel having unknown parameters; processing the thereby obtained spectral raw data to reduce noise and adjust for drift and diffuse light scatter; and applying the developed calibration model on the processed spectral data in order to determine the unknown parameters.

11. A method according to claim 10, characterized in that in (I.c) the multivariate analysis includes transferring the processed reference spectral data into latent variables; and that in (II) the processed spectral data are transferred into latent variables as according to (I.c), and the developed calibration model applied on the latent variables in order to determine the unknown parameters.

12. A method according to claim 11, characterized in that the spectrometeric method is an absorption, reflectance, emission or transmission spectrometric method.

13. A method according to claim 10, characterized in that the spectrometeric method is an absorption, reflectance, emission or transmission spectrometric method.

14. A method according to claim 1, characterized in that the raw wood material or the wood based panel and the reference raw wood material or reference wood based panels are dried to a moisture content of below 8%.

15. A method according to claim 1, characterized in that the raw wood material or the wood based panel and the reference raw wood material or reference wood based panels are dried to a moisture content of below 4%.

16. A method according to claim 1, characterized in that the raw wood material contains surface or core particles, or both.

17. A method according to claim 1, characterized in that the spectrometric method is a NIR spectrometic method.

18. A method according to claim 1, characterized in that the board parameters to be determined are selected from density, density profile, internal bond, thickness swelling, absorption value, permeability value, perforator value, and emission chamber value.

19. A method according to claim 1, characterized in the multivariate analysis is selected from Principal Component Analysis (PCA), Partial Least Squares Regression (PLS), Principal Component Regression (PCR), Multilinear Regression Analysis (MLR) and Discriminant Analysis.

20. A method according to claim 19, characterized in the multivariate analysis as used is Partial Least Squares Regression (PLS).

21. A method for controlling process variables influencing parameters of a wood based panel produced from raw wood material flowing into a process line for production of wood based panels, characterized in that it comprises the steps of analyzing the raw wood material or the wood based panel while having a moisture content of below 10% by a spectrometric method giving spectral data, and comparing said spectral data with reference spectral data obtained by said spectrometric method from reference raw wood material or reference wood based panels produced from said reference raw wood material in a process for production of wood based panels while having a moisture content of below 10%, which reference spectral data have been calibrated to process variables in such a process, by means of multivariate analysis.

22. A method for controlling process variables according to claim 21, characterized in that the spectral data is compared with reference spectral data obtained from reference raw wood material or reference wood based panels produced from said reference raw wood material in a reference process for production of wood based panels which reference spectral data have been calibrated to process variables applied in said reference process.

23. A method for controlling process variables according to claim 21, characterized in that the spectral data is linked into a combination with a desired parameter, and said combination is compared with reference combinations obtained by linking reference spectral data, obtained from reference raw wood material or reference wood based panels, with known parameters of said reference raw wood material or said reference wood based panels, which reference combinations have been calibrated to known process variables by means of multivariate analysis.

24. A method for controlling process according to claim 23, characterized in that the raw wood material is analysed, and the combination is compared with reference combinations obtained by linking reference spectral data with known parameters of said reference raw wood material.

25. A method for controlling process according to claim 23, characterized in that the wood based panel is analysed and the combination is compared with reference combinations obtained by linking reference spectral data with known parameters of said reference wood based panels.

\* \* \* \* \*